United States Patent [19]

Kawanabe et al.

[11] Patent Number: 4,732,127

[45] Date of Patent: Mar. 22, 1988

[54] AIR/FUEL RATIO CONTROL SYSTEM FOR AN INTERNAL COMBUSTION ENGINE WITH A FUNCTION FOR PREVENTING THE BLACKENING PHENOMENON OF OXYGEN CONCENTRATION SENSOR

[75] Inventors: Tomohiko Kawanabe; Masahiko Asakura; Katsuhiko Kimura; Minoru Muroya, all of Wako, Japan

[73] Assignee: Honda Giken Kogyo Kabushiki Kaisha, Tokyo, Japan

[21] Appl. No.: 905,434

[22] Filed: Sep. 10, 1986

[30] Foreign Application Priority Data

Sep. 21, 1985 [JP] Japan .................................. 60-209841

[51] Int. Cl.$^4$ ................................................. F02B 3/00
[52] U.S. Cl. ....................................... 123/440; 123/589
[58] Field of Search .............................. 204/195 S, 1 T; 123/440, 489, 585, 589

[56] References Cited

U.S. PATENT DOCUMENTS

| | | | |
|---|---|---|---|
| 4,354,468 | 10/1982 | Sone | 123/440 |
| 4,363,306 | 12/1982 | Sone | 123/440 |
| 4,365,604 | 12/1982 | Sone | 123/440 |
| 4,538,575 | 9/1985 | Chujo | 123/489 |
| 4,563,991 | 1/1986 | Akatsuka | 123/489 |
| 4,566,419 | 1/1986 | Ninomiya | 123/489 |
| 4,611,562 | 9/1986 | Nakano | 123/489 |

Primary Examiner—Ronald B. Cox
Attorney, Agent, or Firm—Pollock, Vande Sande and Priddy

[57] ABSTRACT

An air/fuel ratio control system for an internal combustion engine having an air supply system for controlling the air/fuel ratio of mixture to be supplied to the engine, and an oxygen concentration sensing device for sensing the oxygen concentration in the exhaust gas of the internal combustion engine. The oxygen concentration sensing device includes a pair of solid electrolyte members operating as an oxygen pump element to which a pump current is supplied, and a sensor cell element. An open/close valve is provided in the air supply system and controlled by a duty ratio control circuit which causes the open/close valve to be opened for a calculated valve open time period in each of successive predetermined cycles in response to a result of detection of air/fuel ratio. When the calculated valve open time period exceeds a predetermined upper limit, the supply of the pump current is stopped so that the blackening phenomenon of the solid electrolyte members is avoided.

2 Claims, 10 Drawing Figures

AIR/FUEL RATIO CONTROL SYSTEM FOR AN INTERNAL COMBUSTION ENGINE WITH A FUNCTION FOR PREVENTING THE BLACKENING PHENOMENON OF OXYGEN CONCENTRATION SENSOR

CROSS REFERENCE TO RELATED APPLICATIONS

Related subject matter is disclosed in Asakura et al U.S. application Ser. No. 843,951 filed Mar. 25, 1985, Kawanabe et al U.S. application Ser. No. 908,854 filed Sept. 18, 1986, and Kawanabe et al U.S. application Ser. Nos. 909,534 and 909,535 filed Sept. 22, 1986, each of which is assigned to the assignee of the instant application.

BACKGROUND OF THE INVENTION

1. Field of the Invention

The present invention relates to an air/fuel ratio control system for an internal combustion engine, and more particularly to an air/fuel ratio control system using a linear type oxygen concentration sensor and having a function for preventing the so-called blackening phenomenon of the oxygen concentration sensor.

2. Description of Background Information

Air/fuel ratio feedback control systems for an internal combustion engine are well known, in which the oxygen concentration in the exhaust gas of the engine is detected by an oxygen concentration sensor and an air/fuel ratio of mixture to be supplied to the engine is feedback controlled in response to a result of the detection of the oxygen concentration so as to purify the exhaust gas and improve the fuel economy.

As an example of this air/fuel ratio control system, a duty ratio control type secondary air supply system has been proposed which is provided with an open/close valve disposed in an air intake side secondary air supply passage leading to the carburetor, downstream of the throttle valve. The open/close valve is controlled in such a manner that a duty ratio between the opening and closing of the open/close valve is controlled in response to an output signal level of the oxygen concentration sensor.

In such an air/fuel ratio control system, a detection operation as to whether the air/fuel ratio of a mixture is lean or rich with respect to a target air/fuel ratio is performed by using the output signal level of the oxygen concentration sensor. When a result of the detection indicates that the air/fuel ratio is lean, a base valve open duration is decreased by a predetermined amount in each duty cycle of valve operation. On the other hand, if the result of detection indicates that the air/fuel ratio of the mixture is rich, the base valve open duration in each duty cycle is increased by a predetermined amount. The thus produced calculation value of an integration control operation is used as an output valve open time duration. The open/close valve is opened for this output valve open time duration.

In another case, a correction value for the integration control operation is decreased by a predetermined value when the result of detection indicates that the air/fuel ratio is lean. When, on the other hand, the result of detection indicates that the air/fuel ratio is rich, the correction value is increased by a predetermined amount. The correction value is then added to a base valve open time duration in each duty cycle. The thus obtained calculation value is used as the output valve open time duration for which the open/close valve is opened in each duty cycle of valve operation.

As an example of an oxygen concentration sensor for use in air/fuel ratio control systems of the above mentioned type, Japanese patent application Laid Open No. 58-153155 discloses an oxygen concentration sensor having an output signal whose level is proportional to the oxygen concentration in a measuring gas (whose oxygen concentration is to be measured) when the air/fuel ratio of the mixture supplied to the engine is larger than a stoichiometric air/fuel ratio. This oxygen concentration sensor includes a pair of flat oxygen-ion conductive solid electrolyte members. The oxygen-ion conductive solid electrolyte members are placed in the atmosphere of an exhaust gas of the engine. Electrodes are respectively provided on the front and back surfaces of both of the solid electrolyte members. In other words, each pair of electrodes sandwich each solid electrolyte member. These two solid electrolyte members each having a pair of electrodes are arranged in face to face relation with each other to form a gap portion between them.

With this arrangement, one of the solid electrolyte members operates as an oxygen pump element and the other one of the solid electrolyte members operates as a sensor cell element for measuring an oxygen concentration ratio. In the atmosphere of the test gas, a drive current is supplied across the electrodes of the oxygen pump element in such a manner that the electrode facing the gap portion is used as a negative electrode. By the supply of this current, the oxygen component of the gas within the gap portion is ionized on the surface of the negative electrode of the oxygen pump element. The oxygen ions migrate through the inside of the oxygen pump element to the positive electrode, where the oxygen ions are released from the surface of the positive electrode in the form of the oxygen gas.

While this movement of oxygen ions is taking place, an electric potential is generated across the electrodes of the sensor cell element because the oxygen concentration of the gas in the gap portion differs from the oxygen concentration of the gas outside the electrodes of the sensor cell element. If the magnitude of the electric current supplied to the oxygen pump element, that is "the pump current", is constant, the electric potential generated across the sensor cell element becomes proportional to the oxygen concentration difference, i.e, the oxygen concentration in the exhaust gas.

By using this electric potential developed across the electrodes of the sensor cell element, the detection is performed as to whether the air/fuel ratio of the mixture supplied to the engine is rich or lean with respect to the target air/fuel ratio. In addition, the target value of air/fuel ratio is determined to be larger than the stoichiometric air/fuel ratio. Further, if the magnitude of the pump current to be supplied to the pump element is varied so that the electric potential across the electrodes of the sensor cell element becomes constant, the magnitude of the pump current becomes substantially proportional to the oxygen concentration in the exhaust gas under a condition of room temperature. Therefore, the air/fuel ratio can be also detected by means of the magnitude of the pump current.

In this type of oxygen concentration sensing devices, if an excessive current is supplied to the oxygen pump element, it causes the so called blackening phenomenon by which the oxygen ions are removed from the solid electrolyte members. For instance, when zirconium dioxide ($ZrO_2$) is utilized as the solid electrolyte, the oxygen ions $O_2$ are taken from the zirconium dioxide ($ZrO_2$) so that zirconium (Zr) is separated out. As a result of this blackening phenomenon, a deterioration of the oxygen pump element takes place rapidly, to cause a debasement of the operation of the oxygen concentration sensor as a whole.

FIG. 1 shows curves indicating current $I_p$ to the oxygen pump element versus oxygen concentration relations and a boundary line of the occurrence of the blackening phenomenon. As illustrated, the magnitude of the current $I_p$ varies in proportion to the oxygen concentration, and the rate of variation is different for several different values of the voltage Vs developing across the electrodes of the sensor cell element. In other words, the voltage Vs is a parameter which determines the relation between the magnitude of the current $I_p$ and the oxygen concentration. As illustrated in this figure, the boundary line of the occurrence of the blackening phenomenon is expressed, as in the case of the magnitude of the current $I_p$, as a first-degree function of the oxygen concentration value. Therefore, for preventing the blackening phenomenon, it is necesssary that the magnitude of the supply current to the oxygen pump element is limited to be smaller than values in the region of the blackening phenomenon.

In air/fuel ratio control systems using this type of oxygen concentration sensing device, the calculated output valve open time may exceed the above mentioned upper limit of the valve open period due to a deviation of a basic air/fuel ratio set value of the carburetor, or when the auxiliary power supply system such as a power valve is in operation, or during an engine operation after a hot start of the engine. If the valve open period exceeds the upper limit of the valve open period, the amount of air flowing through the open/close valve will be saturated. Therefore, under such a condition, the output valve open period is set to be equal to the above mentioned upper limit value of the valve open period. Therefore, the air/fuel ratio of the mixture supplied to the engine is not made lean enough. Under such a condition, the air/fuel ratio is at around a stoichiometric value or a value slightly richer than the stoichiometric value.

However, there is a relation that the richer the air/fuel ratio becomes, or in other words, the smaller the oxygen concentration becomes, the lower becomes the boundary level of the occurrence of the blackening phenomenon. Therefore, under such a condition of the air/fuel ratio, the value of the current supplied to the oxygen pump element is above a critical value of the occurrence of the blackening phenomenon. Thus in conventional arrangements, there has been a chance of occurrence of the blackening phenomenon.

OBJECT AND SUMMARY OF THE INVENTION

An object of the present invention is therefore to provide an air/fuel ratio control system in which the occurrence of the blackening phenomenon is prevented when the output valve open time duration is set at an upper limit of the valve open time.

According to the present invention, the air/fuel ratio control system is so constructed that the supply of the current to the oxygen pump element is stopped when the calculated value of the output valve open time duration becomes longer than the upper limit of the valve open time.

BRIEF EXPLANATION OF THE DRAWINGS

FIG. 6 is a diagram showing the manner in which FIGS. 6A and 6B are combined;

DETAILED DESCRIPTION OF THE PREFERRED EMBODIMENT

Figure 1:
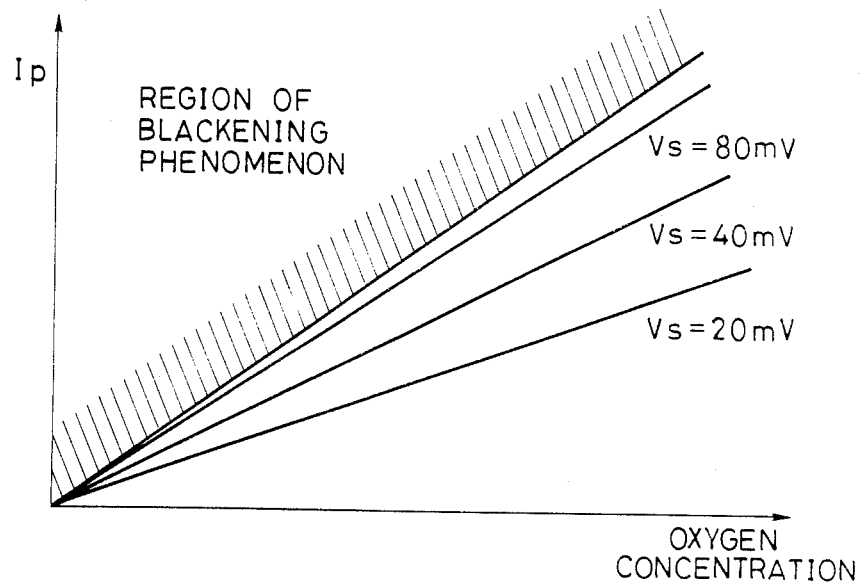
FIG. 1 is a diagram showing the relation between the magnitude of the pump current supplied to the oxygen pump element versus the oxygen concentration, and the boundary of the occurrence of the blackening phenomenon.
Figure 2:
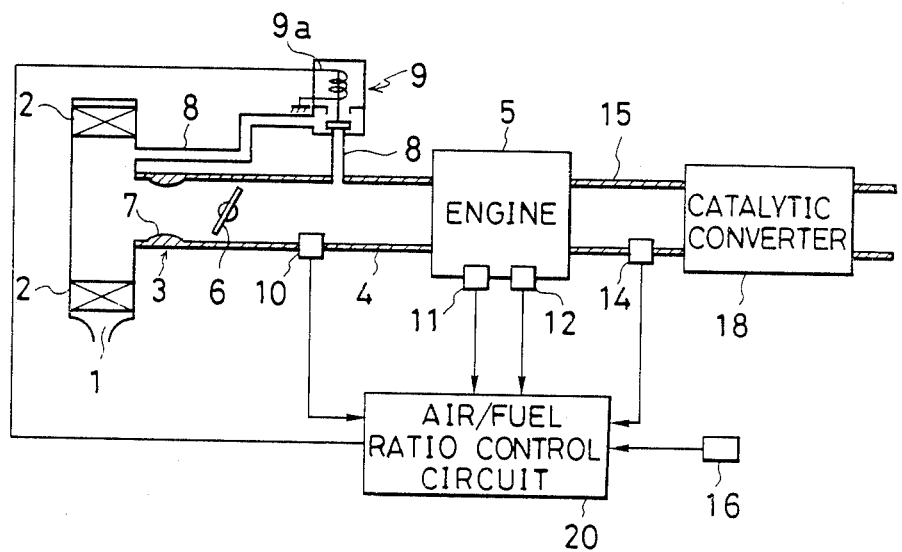
FIG. 2 is a block diagram showing an embodiment of the air/fuel ratio control system according to the present invention.

FIG. 2 schematically shows an internal combustion engine which is provided with an air/fuel ratio control system according to the present invention.

As shown, the air taken at an air inlet port 1 is supplied to an internal combustion engine 5 through an air cleaner 2, a carburetor 3, and an intake manifold 4. The carburetor 3 is provided with a throttle valve 6 and a venturi 7 which is formed upstream of the throttle valve 6.

The inside of the air cleaner 2, near its air outlet port, communicates with the intake manifold 4 through an air intake side secondary air supply passage 8. In the air intake side secondary air supply passage 8, there is provided an open/close solenoid valve 9 which is arranged to open when a drive current is supplied to its solenoid 9a.

The air/fuel ratio control system further includes various sensors such as an absolute pressure sensor 10 provided on the intake manifold 4 for detecting an absolute pressure in the intake manifold 4. The reference numeral 11 indicates a crank angle sensor for generating pulse signals in response to the rotation of a crankshaft (not shown) of the engine 5. The reference numeral 12 indicates a cooling water temperature sensor for generating an output signal whose level is responsive to the temperature of engine cooling water. Similarly, an oxygen concentration sensor 14 is provided in an exhaust manifold 15 of the engine 5, which generates an output signal whose level is proportional to an oxygen concentration in exhaust gas of the engine 5. In the exhaust manifold 15 downstream of the position of the oxygen concentration sensor 14, there is provided a catalytic converter 18 for accelerating the reduction of noxious components in the exhaust gas.

The open/close solenoid valve 9, the absolute pressure sensor 10, the crank angle sensor 11, the cooling water temperature sensor 12 and the oxygen concentration sensor 14 are connected to an air/fuel ratio control circuit 20 to which is also connected a vehicle speed sensor 16 which generates an output signal whose level is responsive to the speed of the vehicle on which the engine is mounted.

Figure 3:
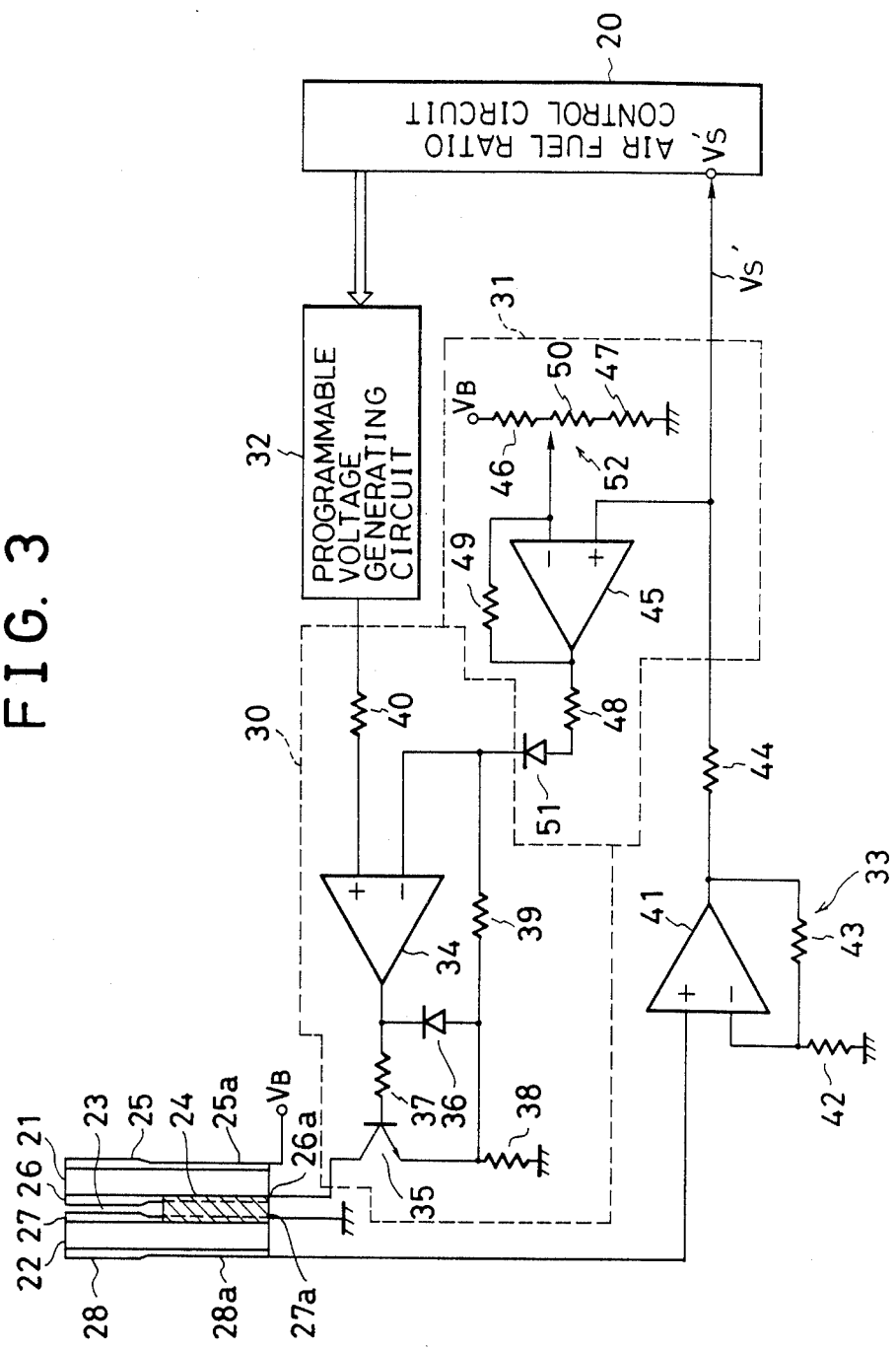
FIG. 3 is a schematic diagram showing the construction of the oxygen concentration sensor used in the system of FIG. 2.

FIG. 3 shows an example of the oxygen concentration sensor used in the air/fuel ratio control system according to the present invention. As shown, the oxygen concentration sensor 14 includes a pair of plate-like elements, namely an oxygen pump element 21 and a sensor cell element 22, which are arranged in parallel to each other. The main portion of the oxygen pump element 21 and the sensor cell element 22, i.e. first and second active plates, are made of an oxygen-ion conductive solid electrolyte member. An end portion of the oxygen pump element 21 and an end portion of the sensor cell element 22 which face each other are spaced apart so as to form gap portion (or in other words, a restricted region) 23 between them. The other end portions of the oxygen pump element 21 and the sensor cell element 22 are connected to each other by means of a spacer 24. The oxygen pump element 21 and the sensor cell element 22 are provided, at their free end portions and on both sides thereof, with square electrodes 25 through 28 which are made of porous heat-proof metal. Further, lead wires 25a through 28a of the electrodes 25 through 28 respectively, are provided on both surfaces of the connected end portions of the oxygen pump element 21 and the sensor cell element 22.

A control part of the oxygen concentration sensor 14 includes a constant current circuit 30, a limiter circuit 31, a programmable voltage generating circuit 32 and a non-inverting amplifier 33. A pump current is supplied between the electrodes 25 and 26 of the oxygen pump element 21 from the constant current circuit 30. The constant current circuit 30 is made up of an operational amplifier 34, an NPN transistor 35, a diode 36, and resistors 37 through 40. More particularly, an output terminal of the operational amplifier 34 is connected to the base of the transistor 35 via the resistor 37. The emitter of the transistor 35 is connected to ground via the resistor 38 and is also connected to an inverting input terminal of the operational amplifier 34 via the resistor 39. The emitter of the transistor 35 is further connected to an output terminal of the operational amplifier 34 through the diode 36 which is arranged in the forward direction. The resistor 38 is provided in order to detect the magnitude of the pump current $I_p$ flowing between the electrodes 25 and 26 of the oxygen pump element 21. The collector of the transistor 35 is connected to the inner electrode 26 of the oxygen pump element 21 through the lead wire 26a. The outer electrode 25 of the oxygen pump element 21 is supplied with an electric current having a voltage $V_B$ through the lead wire 25a.

The non-inverting input terminal of the operational amplifier 34 is connected to the programmable voltage generating circuit 32 via the resistor 40. The programmable voltage generating circuit 32 generates an output signal whose voltage is responsive to an $I_p$ value command data supplied from the air/fuel ratio control circuit 20.

On the other hand, the inner electrode 27 of the sensor cell element 22 is grounded through the lead wire 27a, and the outer electrode 28 of the sensor cell element 22 is connected, through the lead wire 28a, to the non-inverting amplifier 33 which is made up of an operational amplifier 41 and resistors 42 through 44. An output terminal of the noninverting amplifier 33 is connected to a $V_s'$ input terminal of the air/fuel ratio control circuit 20. An output terminal of the non-inverting amplifier 33 is connected to the limiter circuit 31. The limiter circuit 31 is made up of an operational amplifier 45, resistors 46 through 49, a variable resistor 50, and a diode 51. The resistors 46, 47 and the variable resistor 50 are connected in series, to form a voltage divider circuit 52 which provides a divided value of the voltage $V_B$ as a limiter reference voltage signal $V_L$. A terminal of the variable resistor 50 connected to its movable contact, i.e. a terminal of the divided output signal, is connected to the inverting input terminal of the operational amplifier 45. The operational amplifier 45 produces, at its output terminal, a voltage corresponding to a difference between the output signal of the non-inverting amplifier 33 which is supplied to its non-inverting input terminal and the divided voltage from the dividing circuit 52 which is supplied to its inverting input terminal. The output signal of the operational amplifier 45, from its output terminal, is supplied to the inverting input terminal of the operational amplifier 34 through the resistor 48 and the diode 51 which is arranged in the forward direction.

Figure 4:
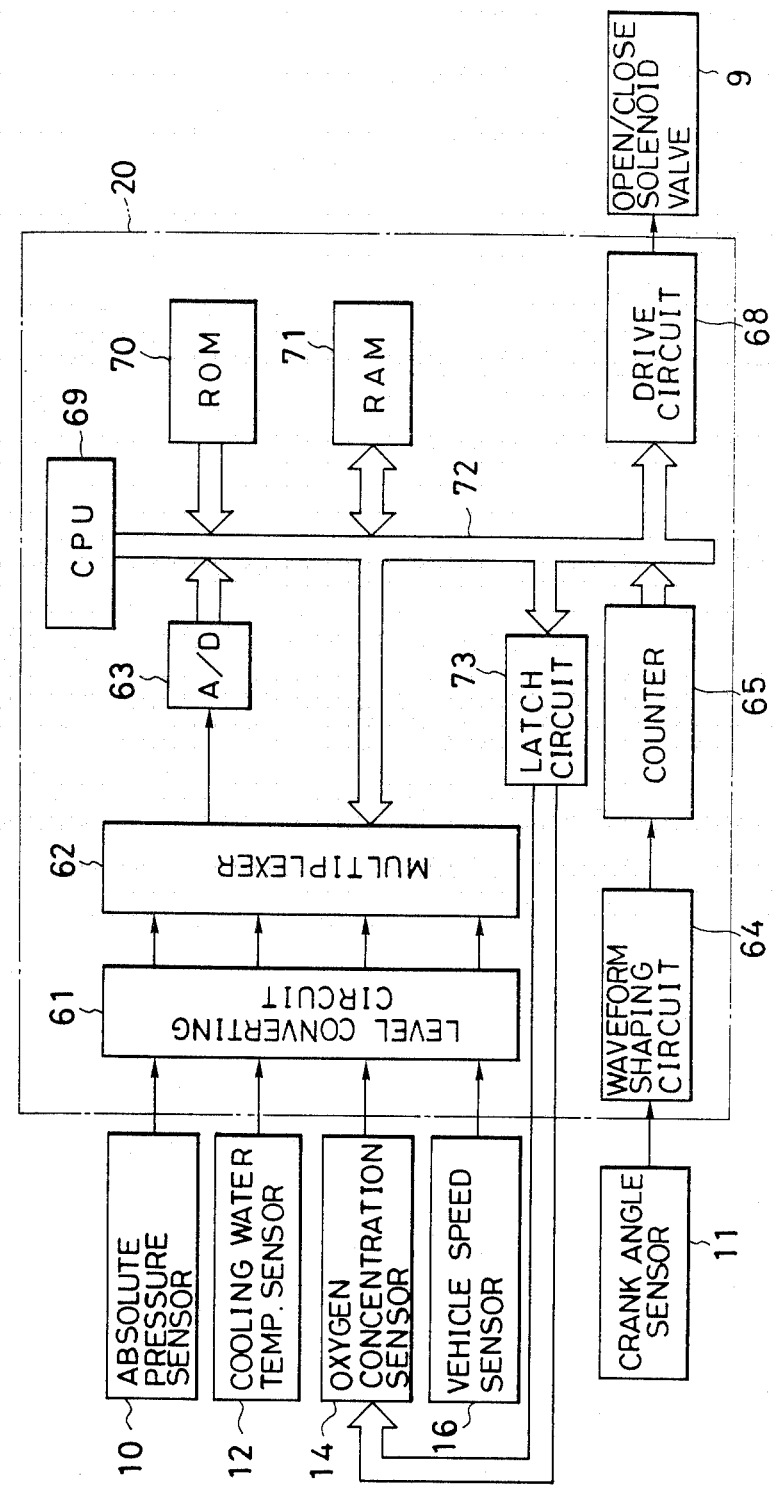
FIG. 4 is a block diagram showing the construction of the control circuit 20 of the system of FIG. 2.

FIG. 4 shows the construction of the control circuit 20. As shown, the control circuit 20 includes a level converting circuit 61 which effects a level conversion of the output signals of the absolute pressure sensor 10, the engine cooling water temperature sensor 12, the oxygen concentration sensor 14, and the vehicle speed sensor 16. Output signals provided from the level converting circuit 61 are in turn supplied to a multiplexer 62 which selectively outputs one of the output signals from each sensor passed through the level converting circuit 61. The output signal provided by the multiplexer 62 is then supplied to an A/D converter 63 in which the input signal is converted into a digital signal. The control circuit 20 further includes a waveform shaping circuit 64 for a waveform shaping of the output signal of the crank angle sensor 11, to provide TDC signals in the form of pulse signals. The TDC signals from the waveform shaping circuit 64 are in turn supplied to a counter 65 which counts intervals of the TDC signals. The control circuit 20 includes a drive circuit 68 for driving the open/close solenoid valve 9, a CPU (central processing unit) 69 which performs digital operations according to various programs, a ROM 70 in which various operating programs and data are previously stored, a RAM 71, and a latch circuit 73 for holding the $I_p$ value command data. The multiplexer 62, the A/D converter 63, the counter 65, the drive circuit 68, the CPU 69, the ROM 70, the RAM 71, and the latch circuit 73 are mutually connected via an input/output bus 72.

With this circuit construction, when the $I_p$ command data is supplied from the air/fuel ratio control circuit 20 to the programmable voltage generating circuit 32, the latter circuit in turn supplies a signal whose voltage corresponds to the $I_p$ command data to the non-inverting input terminal of the operational amplifier 34 through the resistor 40 as a reference voltage $V_{r1}$.

The pump current $I_p$ flowing between the electrodes 25 and 26 of the oxygen pump element 21 is detected by using a voltage $V_p$ appearing across terminals of the resistor 38. This terminal voltage $V_p$ of the resistor 38 is supplied to the inverting input terminal of the operational amplifier 34 through the resistor 39. When the terminal voltage $V_p$ is lower than the reference voltage $V_{r1}$, the operational amplifier 34 produces a high level output signal which in turn increases the base current of the transistor 35. As a result, the pump current increases. On the other hand, when the terminal voltage $V_p$ is equal to or greater than the reference voltage $V_{r1}$, the output signal level of the operational amplifier 34 turns low, to decrease the base current of the transistor 35. The pump current is decreased under this condition. Since the above two operations are repeated at a high speed, the pump current becomes stable at a constant current level corresponding to the reference voltage $V_{r1}$, i.e. the $I_p$ value command data.

On the other hand, a voltage Vs appears across the electrodes 27 and 28 of the sensor cell element 22. The voltage Vs is amplified in voltage by the non-inverting amplifier 33 and supplied to the air/fuel ratio control circuit 20 as an output voltage Vs' of the oxygen concentration sensor 14.

Assuming that the air/fuel ratio of the mixture supplied to the engine is varying at around the stoichiometric air/fuel ratio, the voltage Vs across the electrodes 27 and 28 of the sensor cell element 22 rises. This causes a rise in the level of the output signal Vs' of the non-inverting amplifier 33. If the level of the output signal Vs' of the non-inverting amplifier 33 goes up and exceeds the limiter reference voltage $V_L$, a voltage corresponding to a difference between the output signal Vs' and the limiter reference voltage $V_L$ which is obtained by the operational amplifier 45 becomes higher than the terminal voltage $V_p$. Therefore, from the output terminal of the operational amplifier 45, a current flows through the resistor 48, the diode 51, the resistor 39, and the resistor 38. This current raises the voltage level of the inverting input terminal of the operational amplifier 34 to a value higher than the reference voltage Vr1. Therefore, the output signal level of the operational amplifier 34 is lowered and the base current of the transistor 35 is decreased. In this way, the pump current $I_p$ of the oxygen pump element 21 is decreased.

Since the limiter reference voltage $V_L$ is set at a level slightly higher than the output signal level Vs' under a condition of target air/fuel ratio, it indicates that the operation of the system is approaching to the region of the occurrence of blackening phenomenon when the output voltage Vs' of the noninverting amplifier 33 reaches the limiter reference voltage $V_L$. Moreover, if Vs'>$V_L$, the level of the output signal of the operational amplifier 45 rises as the air/fuel ratio becomes rich, to decrease the pump current $I_p$. In this way, the blackening phenomenon is prevented.

In the air/fuel ratio control circuit 20, information regarding the absolute pressure in the intake manifold 4, the engine cooling water temperature, the oxygen concentration in the exhaust gas, and the vehicle speed is selectively supplied from the A/D converter 63 to the CPU 69 via the input/output bus 72. Also, information indicative of the engine speed is supplied from the counter 65 to the CPU 69 via the input/output bus 72. The CPU 69 is constructed to generate an internal interruption signal every one duty period. In response to this internal interruption signal, the CPU 69 performs an operation for the duty ratio control of the air intake side secondary air supply, explained hereinafter.

Figure 5:
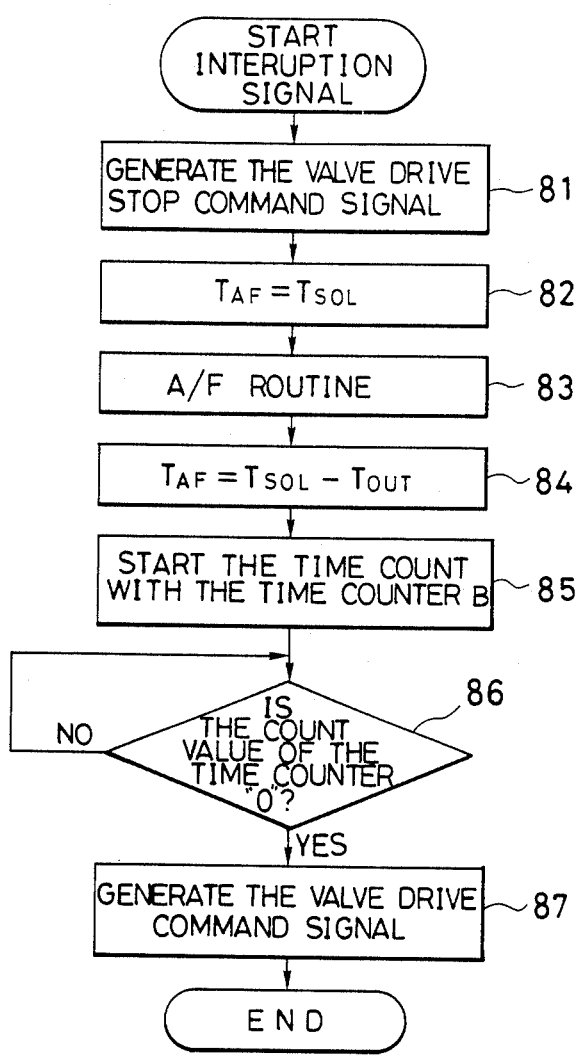
FIG. 5 is a flowchart showing the manner of operation of a CPU 69 in the control circuit 20.
Figure 6A:
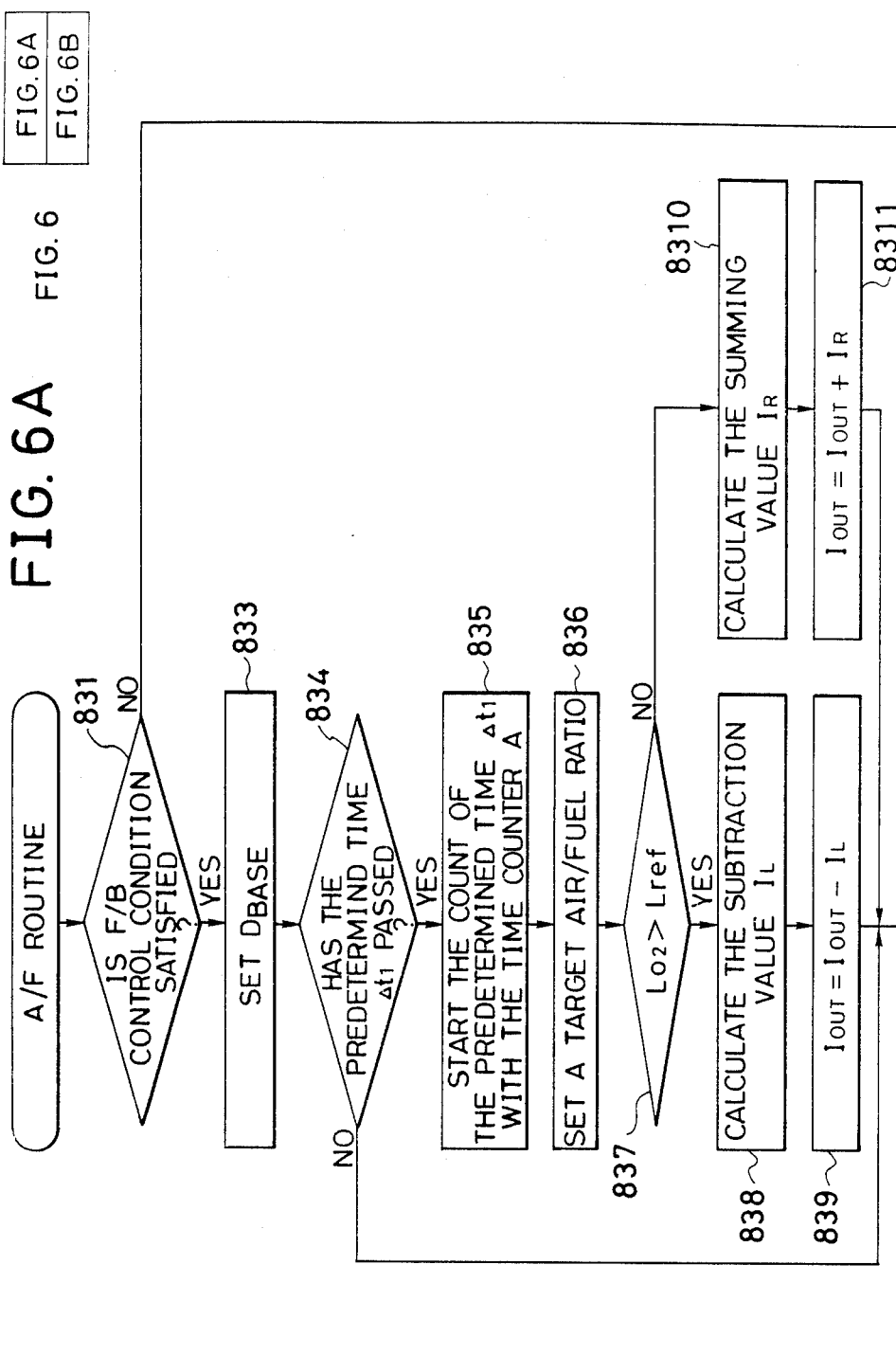
FIGS. 6A and 6B, when combined, are a flowchart showing the A/F routine of FIG. 5.
Figure 6B:
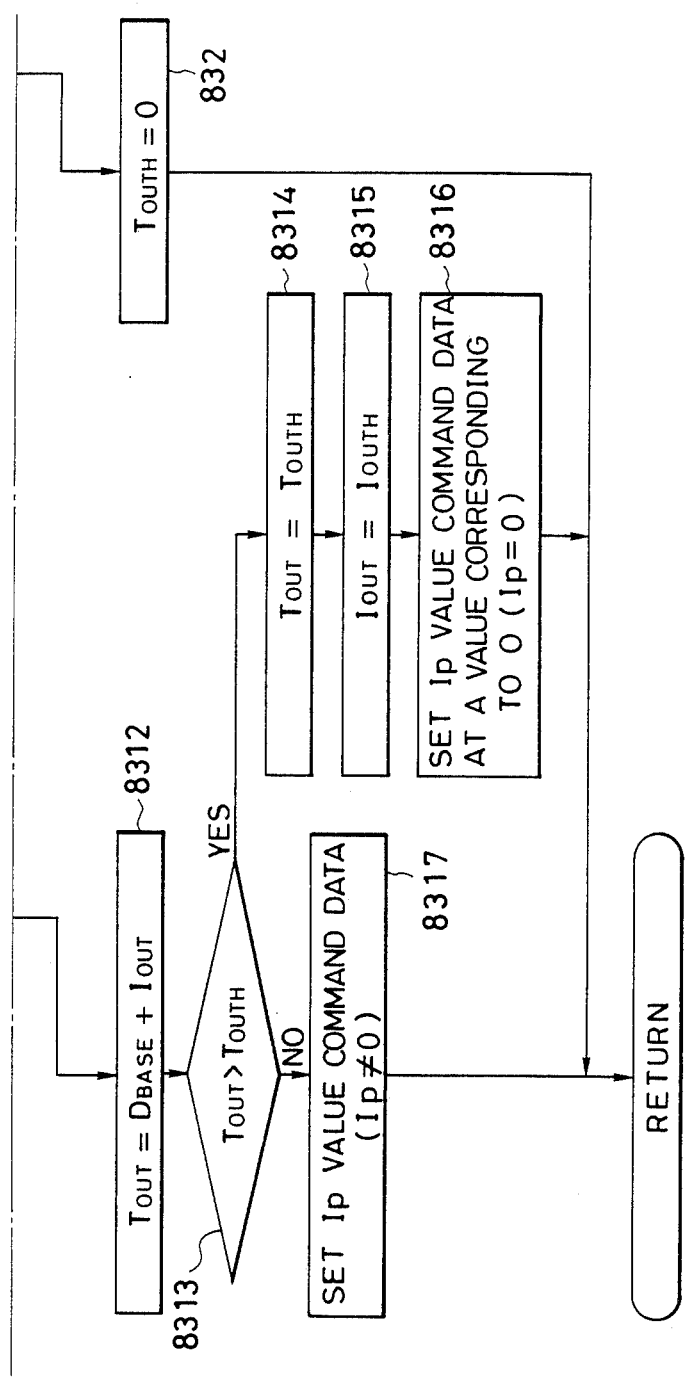

Referring to the flowcharts of FIGS. 5 and 6 showing the operation of the CPU 69, the operation of the air/fuel ratio control system according to the present invention will be explained hereinafter.

At a step 81, a valve open drive stop command signal is generated in the CPU 69 and supplied to the drive circuit 68, every time of generation of the internal interruption signal in the CPU 69. With this signal, the drive circuit 68 is controlled to close the open/close solenoid valve 9. This operation is provided so as to prevent malfunctions of the open/close solenoid valve 9 during the calculating operation of the CPU 69. Next, a valve close period $T_{AF}$ of the open/close solenoid valve 9 is made equal to a period of one duty cycle $T_{SOL}$ at step 82, and an A/F routine for calculating a valve open period $T_{OUT}$ of the open/close solenoid valve 9 which is shown in FIG. 6 is carried out through steps generally indicated at 83.

Figure 7:
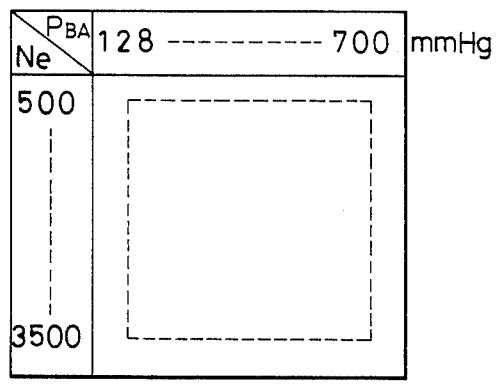
FIG. 7 is a diagram showing a data map which is previously stored in a ROM 70 of the control circuit 20.

In the A/F routine, whether or not operating states of the vehicle (including operating states of the engine) satisfy a condition for the feedback (F/B) control is detected at a step 831. This detection is performed according to various parameters, i.e., the absolute pressure within the intake manifold, the engine cooling water temperature, the vehicle speed, and the engine rotational speed. For instance, when the vehicle speed is low, or when the engine cooling water temperature is low, it is determined that the condition for the feedback control is not satisfied. If it is determined that the condition for the feedback control is not satisfied, the valve open period $T_{OUT}$ is made equal to "0" at a step 832 to stop the air/fuel ratio feedback control. On the other hand, if it is determined that the condition for the feedback control is satisfied, the supply of the secondary air within the period of one duty cycle $T_{SOL}$, i.e., a period of base duty ratio $D_{BASE}$ for the opening of the open/close solenoid valve 9 is set at a step 833. Various values of the period of base duty ratio $D_{BASE}$ which are determined according to the absolute pressure within the intake manifold $P_{BA}$ and the engine speed $N_e$ are previously stored in the ROM 70 in the form of a $D_{BASE}$ data map as shown in FIG. 7, and the CPU 69 first reads current values of the absolute pressure $P_{BA}$ and the engine speed $N_e$ and in turn searches for a value of the period of base duty ratio $D_{BASE}$ corresponding to the read values from the $D_{BASE}$ date map in the ROM 70. Then, whether or not a count period of a time counter A incorporated in the CPU 69 (not shown) has reached a predetermined time period $\Delta t_1$ is detected at a step 834. This predetermined time period $\Delta t_1$ corresponds to a delay time from a time of the supply of the air intake side secondary air to a time in which a result of the supply of the air intake side secondary air is detected by the oxygen concentration sensor 14 as a change in the oxygen concentration of the exhaust gas. When the predetermined time period $\Delta t_1$ has elapsed after the time counter A is reset to start the counting of time, the counter is reset again, at a step 835, to start the counting of time from a predetermined initial value. In other words, a detection as to whether or not the predetermined time period $\Delta t_1$ has passed after the start of the counting of time from the initial value by the time counter A, i.e. the execution of the step 835, is performed at the step 834.

After the start of the counting of the predetermined time period $\Delta t_1$ by the time counter A in this way, a target air/fuel ratio which is leaner than the stoichiometric air/fuel ratio is set at a step 836. For the setting of the target air/fuel ratio, various values for a reference level Lref corresponding to the target air/fuel ratio which is determined according to the values of the absolute pressure within the intake manifold $P_{BA}$ and the engine speed $N_e$ as in the case of the $D_{BASE}$ data map, are previously stored in the ROM 70 as an A/F data map. Therefore, the CPU 69 searches a reference level Lref corresponding to the current values of the absolute pressure $P_{BA}$ and the engine speed $N_e$ from the A/F data map. Next, from the information of the oxygen concentration, whether or not an output signal level $LO_2$ of the oxygen concentration sensor 14 is greater than the reference level Lref determined at the step 836 is detected at a step 837. In other words, whether or not an air/fuel ratio of the mixture to be supplied to the engine 5 is leaner than the target air/fuel ratio is detected at the step 837. If $LO_2 > Lref$, it means that the air/fuel ratio of the mixture is leaner than the target air/fuel ratio, and a subtraction value $I_L$ is calculated at a step 838. The subtraction value $I_L$ is obtained by multiplication among a constant $K_1$, the engine speed $N_e$, and the absolute pressure $P_{BA}$, ($K_1 \cdot N_e \cdot P_{BA}$), and is dependent on the amount of the intake air of the engine 5. After the calculation of the subtraction value $I_L$, a correction value $I_{OUT}$ which is previously calculated by the execution of operation of the A/F routine is read out from a memory location a1 in the RAM 71. Subsequently, the subtraction value $I_L$ is subtracted from the correction value $I_{OUT}$, and a result is in turn written in the memory location a1 of the RAM 71 as a new correction value $I_{OUT}$, at a step 839. On the other hand, if $LO_2 \leq Lref$ at the step 837, it means that the current air/fuel ratio of the mixture is richer than the target air/fuel ratio, and a summing value $I_R$ is calculated at a step 8310. The summing value $I_R$ is calculated by a multiplication among a constant value $K_2$ ($\neq K_1$), the engine speed $N_e$, and the absolute pressure $P_{BA}$ ( $K_2 \cdot N_e \cdot P_{BA}$), and is dependent on the amount of the intake air of the engine 5. After the calculation of the summing value $I_R$, the correction value $I_{OUT}$ which is previously calculated by the execution of the A/F routine is read out from the memory location a1 of the RAM 71, and the summing value $I_R$ is added to the read out correction value $I_{OUT}$. A result of the summation is in turn stored in the memory location a1 of the RAM 71 as a new correction value $I_{OUT}$ at a step 8311. After the calculation of the correction value $I_{OUT}$ at the step 839 or the step 8311 in this way, the correction value $I_{OUT}$ and the period of basic duty ratio $D_{BASE}$ set at the step 833 are added together, and a result of addition is used as the valve open period $T_{OUT}$ at a step 8312.

Subsequently, whether or not the valve open period $T_{OUT}$ is longer than a maximum limit of valve open period $T_{OUTH}$, is detected at a step 8313. The maximum limit of valve open period $T_{OUTH}$ is calculated by an equation $T_{OUTH} = D_{BASE} + K_3 \cdot I_{OUTH}$, where $K_3$ is a coefficient, and $I_{OUTH}$ is a first standard value obtained by multiplication among the engine speed $N_e$, the absolute pressure $P_{BA}$, and a coefficient $\alpha_1$, ($\alpha_1 \cdot N_e \cdot P_{BA}$). If $T_{OUT} > T_{OUTH}$, the output valve open period $T_{OUT}$ is made equal to the maximum limit of valve open period $T_{OUTH}$ at a step 5314, and the correction value $I_{OUT}$ is made equal to a first standard value $I_{OUTH}$ at a step 8315.

Under this condition, it is possible that the blackening phenomenon occurs. The content of $I_p$ value command data which is to be supplied to the programmable voltage generation circuit 32 is made equal to zero ($I_p = 0$) so as to stop the supply of the pump current, at a step 8316. This is, for example, performed by setting a value "0000" in case that the $I_p$ value command data is a four bit data. By this $I_p$ value command data, the reference voltage Vr1 is made equal to zero (0V), and the output signal level of the operational amplifier 34 becomes low. This turns the transistor 35 off to stop the flow of the pump current between the electrodes 25 and 26 of the oxygen pump element 21.

If, $T_{OUT} \leq T_{OUTH}$, the output valve open period $T_{OUT}$ calculated at the step 8312 is maintained as it is, and the value of the $I_p$ value command data to be supplied to the programmable voltage generator circuit 32 is made equal to a predetermined value (not equal to zero) for the detection of oxygen concentration at a step 8317.

Additionally, after the reset of the time counter A and the start of the counting from the initial value at the step 835, if it is detected that the predetermined time period $\Delta t_1$ has not passed at the step 834, the operation of the step 8312 is immediately executed. In this case, the correction value $I_{OUT}$ calculated by the A/F routine up to the previous cycle is read out.

After the completion of the A/F routine, a valve close period $T_{AF}$ is calculated by subtracting the valve open period $T_{OUT}$ from the period of one duty cycle $T_{SOL}$, at a step 84. Subsequently, a value corresponding to the valve close period $T_{AF}$ is set in a time counter B incorporated in the CPU 29 (not shown), and down counting of the time counter B is started at a step 85. Then whether or not the count value of the time counter B has reached a value "0" is detected at a step 86. If the count value of the time counter B has reached the value "0", a valve open drive command signal is supplied to the drive circuit 68 at a step 87. In accordance with this valve open drive command signal, the drive circuit 68 operates to open the open/close solenoid valve 9. The opening of the open/close solenoid valve 9 is continued until a time at which the operation of the step 81 is performed again. If, the step 86, the count value of the time counter B has not reached the value "0", the step 86 is effected repeatedly.

Figure 8:
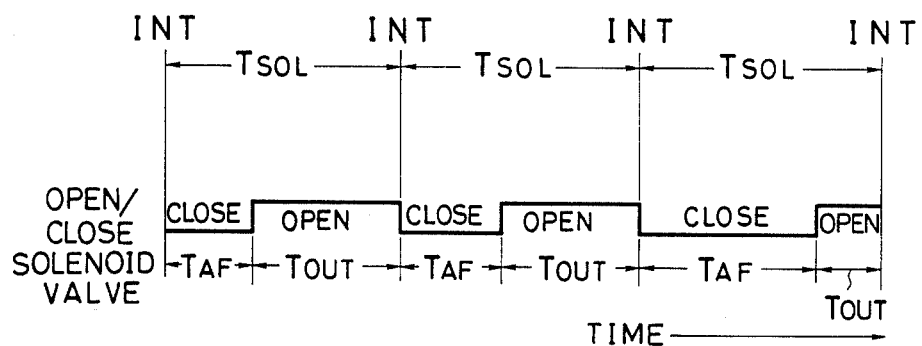
FIG. 8 is a timing chart showing the manner of operation of the system according to the invention generally shown in FIG. 2.

Thus, in the air/fuel ratio control system according to the present invention, the open/close solenoid valve 9 is closed immediately in response to the generation of the internal interruption signal INT as illustrated in FIG. 8, to stop the supply of the air intake side secondary air to the engine 5. When the valve close time $T_{AF}$ for the open/close solenoid valve 9 within the period of one duty cycle is calculated and the valve close time $T_{AF}$ has passed after the generation of the interruption signal, the open/close solenoid valve 9 is opened to supply the air intake side secondary air to the engine through the air intake side secondary air supply passage 8. Thus, the duty ratio control of the supply of the air intake side secondary air is performed by repeatedly executing these operations. In this way, the air/fuel ratio of the mixture to be supplied to the engine is controlled toward the target air/fuel ratio by the duty ratio control of the supply of the air intake side secondary air. It is to be noted that the response characteristic against the command of the supply of the air intake side secondary air and the accuracy of the air/fuel ratio control are also very much improved. Further, the delay of the control response is compensated for by determining the base duty ratio $D_{BASE}$ in response to the operating condition of the engine.

In the embodiment explained so far, the time counter B was incorporated in the CPU 69. However, it is to be noted that the arrangement is not limited to this, and for instance, the time counter B can be provided outside the CPU 69 and the system can be constructed to provide a valve open drive command signal from the time counter B to the drive circuit 68 when the count value of the time counter B has reached "0".

It will be appreciated from the foregoing, according to the present invention, the supply of the current to the oxygen pump element is stopped when the calculated output valve open period becomes longer than the upper limit of the valve open period of the open/close valve. Therefore, the occurrence of the blackening phenomenon is avoided under this condition by setting the output valve open time period at the upper limit of the valve open time period. Thus, the rapid deterioration of the oxygen pump element, which was unavoidable in the conventional arrangement, is prevented.

What is claimed is:

1. An air/fuel ratio control system for an internal combustion engine, comprising:
    an air supply passage connected to an air intake system of said internal combustion engine, for varying the air/fuel ratio of the mixture to be supplied to the engine;
    an open/close valve disposed in said air supply passage for controlling the air flow in said air supply passage;
    an oxygen concentration sensing unit disposed in an exhaust gas of the internal combustion engine, said sensing unit including an oxygen pump element and a sensor cell element which define a diffusion restricted region therebetween, each of said elements including a solid electrolyte member having oxygen ion permeability and a pair of electrodes sandwiching said electrolyte member therebetween;
    current supply means for supplying a pump current across the electrodes of said oxygen pump element so as to keep constant voltage generated across the electrodes of said sensor cell element thereby causing said sensing unit to monitor a magnitude of said pump current which is substantially in proportion to the oxygen concentration in the exhaust gas;
    valve open time period control circuit means connected to said oxygen concentration detection device, for determining the oxygen concentration of the mixture supplied to the engine by means of the magnitude of said pump current and calculating the open time period of said open/close valve in each of a plurality of cyclic periods in response to the result of said determination every cyclic period;
    valve drive means connected to said valve open time period control circuit means for opening said open/close valve for said calculated valve open time period in each of said cycles; and
    control means responsive to output signals of said current supply means and said valve open time period control circuit means for stopping the supply of said pump current across the electrodes of said oxygen pump element when the valve open time period calculated by said valve open time period control circuit means exceeds a predetermined upper limit of valve open time period.

2. An air/fuel ratio control system for an internal combustion engine, comprising:
    a fluid supply passage for varying the air/fuel ratio of the mixture to be supplied to the engine;
    an open/close valve disposed in said fluid supply passage for controlling the fluid flow in said fluid supply passage;
    an oxygen concentration sensing unit disposed in an exhaust gas of the internal combustion engine, said sensing unit including an oxygen pump element and a sensor cell element which define a diffusion restricted region therebetween, each of said elements including a solid electrolyte member having oxygen ion permeability and a pair of electrodes sandwiching said electrolyte member therebetween;
    current supply means for supplying a pump current across the electrodes of said oxygen pump element so as to keep constant a voltage generated across the electrodes of said sensor cell element thereby causing said sensing unit to monitor a magnitude of said pump current which is substantially in proportion to the oxygen concentration in the exhaust gas;
    valve open time period control circuit means connected to said oxygen concentration detection device for determining the oxygen concentration of the mixture supplied to the engine by means of the magnitude of said pump current and calculating the open time period of said open/close valve in each of a plurality of cyclic periods in response to the result of said determination every cyclic period;
    valve drive means connected to said valve open time period control circuit means for opening said open/close valve for said calculated open time period in each of said cycles; and
    control means responsive to output signals of said current supply means and said valve open time period control circuit means for stopping the supply of said drive current across the electrodes of said oxygen pump element when the valve open time period calculated by said valve open time period control circuit means exceeds a predetermined upper limit of valve open time period.

* * * * *